United States Patent
Masuyama et al.

(12) 
(10) Patent No.: US 6,284,243 B1
(45) Date of Patent: *Sep. 4, 2001

(54) PHYSIOLOGICALLY FUNCTIONAL FOOD HAVING BRAIN FUNCTION-IMPROVING, LEARNING ABILITY-ENHANCING, AND MEMORY-ENHANCING FUNCTIONS

(75) Inventors: Akihiro Masuyama; Masaaki Yasui, both of Kanagawa; Hidehiko Yokogoshi, Shizuoka; Masahiko Nomura, Tokyo, all of (JP)

(73) Assignee: Calpis Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/677,935

(22) Filed: Jul. 10, 1996

(30) Foreign Application Priority Data

Jul. 14, 1995 (JP) .................................... 7-178713

(51) Int. Cl.$^7$ ............................. A23C 9/12; A01N 63/00; A23L 1/31; C12N 1/00
(52) U.S. Cl. ......................... 424/93.45; 426/34; 426/56; 426/61; 426/62; 435/170; 435/252.9; 435/823; 435/853; 424/195.16
(58) Field of Search ................................ 426/34, 56, 61, 426/62; 424/93.45, 195.1; 435/170, 252.9, 822, 853

(56) References Cited

U.S. PATENT DOCUMENTS

| | | | |
|---|---|---|---|
| 5,149,535 | 9/1992 | Meinhardt et al. | 424/195.1 |
| 5,563,069 | * 10/1996 | Yang | 435/295.3 |
| 5,691,324 | * 11/1997 | Sandyk | 514/159 |

FOREIGN PATENT DOCUMENTS

| | | |
|---|---|---|
| 2165655 | 7/1972 | (DE) . |
| 0357162 | 3/1990 | (EP) . |
| 2489098 | 3/1982 | (FR) . |
| 0061946 | 10/1982 | (FR) . |
| 1512890 | 6/1978 | (GB) . |

OTHER PUBLICATIONS

Nokanishi et al, "Studies on Lactose–Ferm. Yeasts. X. Free AA. in the . . . Ferm. Milk Beverages", Jap J. of Dairy Sci., Abstr. p. A105–A109, 1973.*
Park et al, "Tryptophan Depl. in Normal Volunteers Prod. Select. Impairments in Learning & Memory", Neuropharmacology 33 (3–4). p 575–588, Abstr. Provided. 1994.*
Gobbetti et al, "The Sourdough Microflora, . . . ", Applied Microbiol. and Biotech. 41 (4) 1994, See Abstract Only.*
Gobbetti et al, "The Sourdough . . . ", World J. of Microbiol. & Biotech, 10 (3). 1994. 275–279. See Abstract Only.*
Kennes et al, "Fermentation of Citrate by Lactobacillus" . . . , Appl. Microbiol Biot. 35(3). 1991. See Abstr. Only.*
Kosikowski: "Cheese and Fermented Milk Foods", 1970, pp. 28–36.
Patent Abstracts of Japan, vol. 17, No. 270, May 26, 1993, & JP 05 009124 (Calpis Food Ind Co Ltd), Jan. 19, 1993.

* cited by examiner

Primary Examiner—Michael G. Wityshyn
Assistant Examiner—Deborah K. Ware
(74) Attorney, Agent, or Firm—Nixon & Vanderhye

(57) ABSTRACT

A physiologically functional food having brain function-improving, learning ability-enhancing and memory-enhancing functions, which comprises as an active ingredient a lactic acid bacterium fermented milk, a lactic acid bacterium and yeast co-fermented milk, or a treated product thereof, or a mixture thereof, optionally also including a pharmaceutically or nutritionally acceptable carrier or diluent.

3 Claims, 3 Drawing Sheets

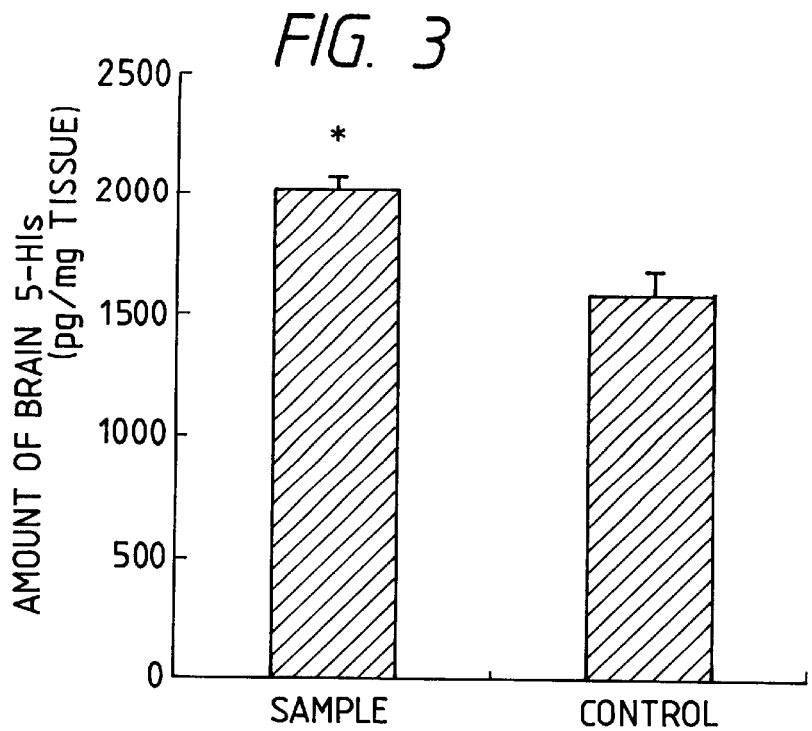
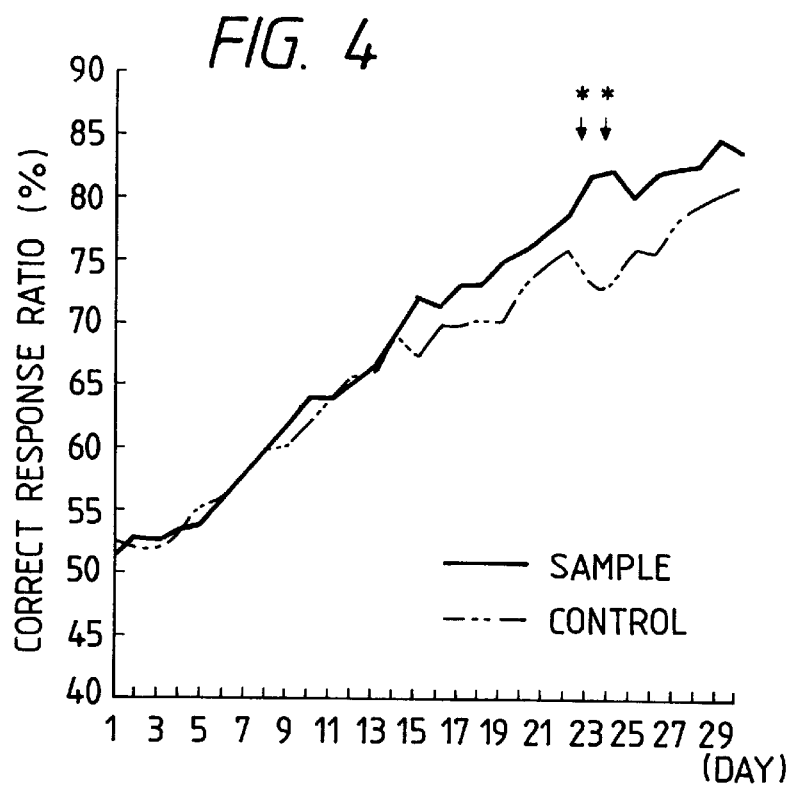

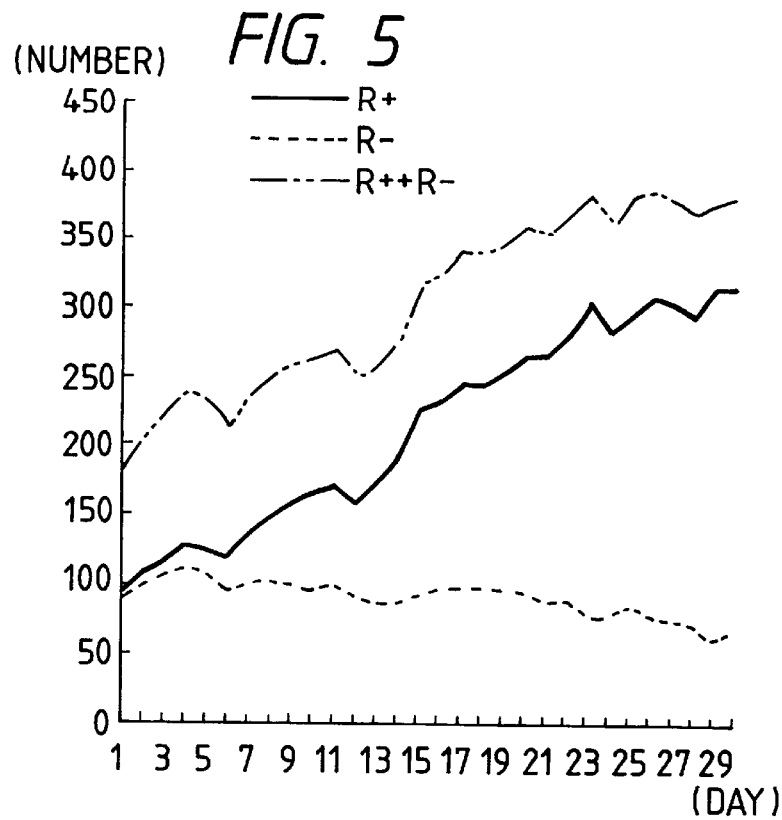
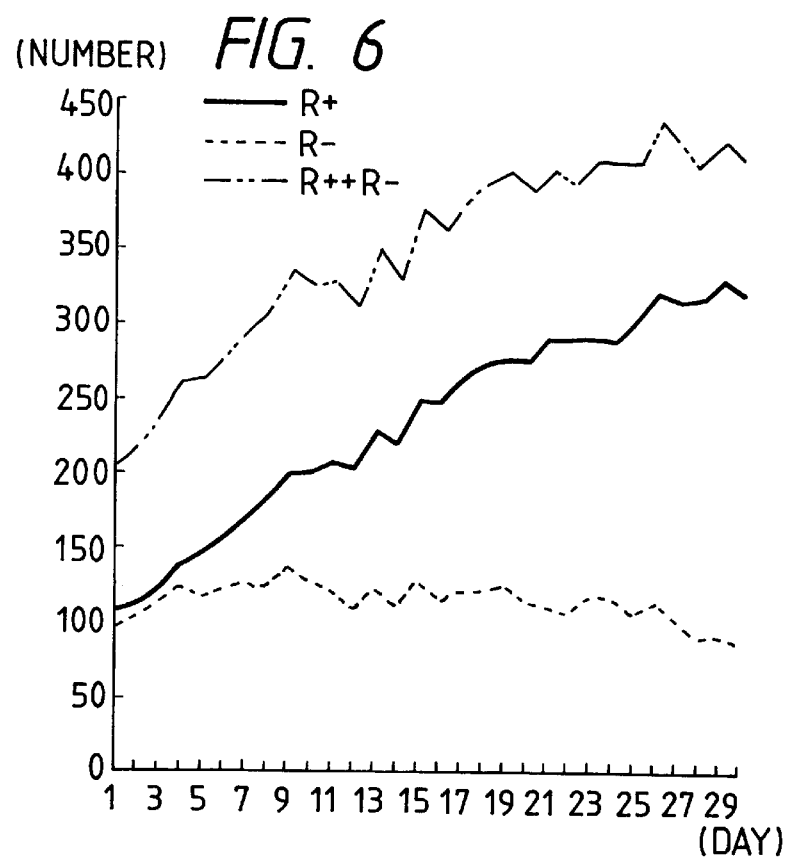

PHYSIOLOGICALLY FUNCTIONAL FOOD HAVING BRAIN FUNCTION-IMPROVING, LEARNING ABILITY-ENHANCING, AND MEMORY-ENHANCING FUNCTIONS

FIELD OF THE INVENTION

The present invention relates to a physiologically functional food having brain function-improving, learning ability-enhancing, and memory-enhancing functions.

BACKGROUND OF THE INVENTION

In recent years, attempts have been made in various fields to investigate substances which enhance brain functions such as learning ability and memory. According to these attempts, the brain function-improving methods so far studied are roughly divided into brain energy metabolism-improving methods in which the action of brain cells is activated through efficient absorption of nutriment into the cells and brain circulation improving methods in which brain cells are supplied with sufficient nutrients and oxygen by improving brain blood circulation. These studies are in progress and drugs having respective pathological actions and therapeutic methods using such drugs are being developed.

On the other hand, α-linolenic acid and docosahexaenoic acid are known as natural food components which have learning function improving effect. It is known that administration of α-linolenic acid improves the correct response ratio in a rat brightness-discrimination learning test (*Seikagaku* (*Biochemistry*), vol.59, p.1235, 1987) and administration of docoeahexaenoic acid improves the same in a rat Y labyrinthine light and shadow discrimination feeding test (JP-A-1-279827; the term "JP-A" as used herein means an "unexamined published Japanese patent application").

From the standpoint, of the positive incorporation of functions of natural food components, social concern has been directed in recent years toward the development of food products which are designed and processed in such a fashion that their functions can be expressed fully in the living body. Also, because of the increasing aged population, great concern has been directed increasingly toward the development of physiologically functional foods having such functions.

SUMMARY OF THE INVENTION

An object of the present invention is to provide a highly safe, physiologically functional food which can improve brain functions in response to the above demands, thereby effecting learning ability-enhancing and memory-enhancing functions.

This and other objects of the present invention have been attained by a physiologically functional food having brain function-improving, learning ability-enhancing and memory-enhancing functions, which comprises as an active ingredient or ingredients a lactic acid bacterium fermented milk, a lactic acid bacterium and yeast co-fermented milk, or a treated product, or a mixture thereof, optionally also including a pharmaceutically or nutritionally acceptable carrier or diluent.

Furthermore, this and other objects of the present invention have been attained by a method for improving brain function or enhancing learning ability or memory comprising administering to human or animals in need of such improvement or enhancement an effective amount of a physiologically functional food which comprises a lactic acid bacterium fermented milk, a lactic acid bacterium and yeast co-fermented milk, or a treated product thereof, or a mixture thereof.

BRIEF DESCRIPTION OF THE DRAWING

FIG. 3 is a graph of total brain hydroxyindole content in sample and control groups in Example 1;

FIG. 4 is a graph of correct response ratios in test feed and control feed groups in the brightness-discrimination learning test of Example 2;

FIG. 5 is a graph of the number of correct response reactions and incorrect response reactions in the test feed group in the brightness-discrimination learning test of Example 2; and FIG. 6 is a graph of the number of correct response reactions and incorrect response reactions in the control feed group In the brightness-discrimination learning test of Example 2.

DETAILED DESCRIPTION OF THE INVENTION

Figure 1:
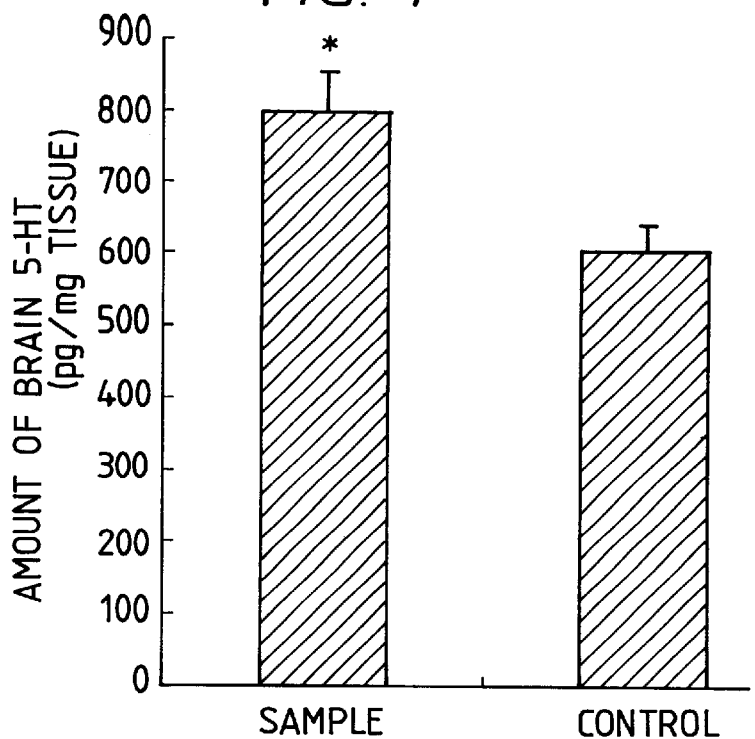
FIG. 1 is a graph of brain serotonin content in sample and control groups in Example 1.

The brain function-improving, learning ability-enhancing and memory-enhancing functions according to the present invention can be confirmed by measuring increased amounts of a brain neurotransmitter, serotonin, after ingesting the physiologically functional food of the present invention. It is well known that brain function-improving effects can be confirmed by the measurement of serotonin content, For example, it has been reported that the brain serotonin content was decreased and learning ability was disturbed in experimental animals when reared with a feed containing corn protein as a nitrogen source which lacked the serotonin precursor tryptophan; on the other hand, the brain serotonin content was increased and the learning ability was improved when the feed was supplemented with tryptophan (*J. Neurochem.*, vol.41 (Suppl.), p.104 (1983), and *Agric. Biol. Chem.*, 52 (3), 701–703 (1988)).

The physiologically functional food of the present invention contains as the active ingredient a lactic acid bacterium fermented milk, a lactic acid bacterium and yeast co-fermented milk, or a treated product thereof, or a mixture thereof, The lactic acid bacterium fermented milk or a lactic acid bacterium and yeast co-fermented milk can be obtained by fermenting milk or a milk component (e.g., whole milk, skim milk, whey) of animal milk, soybean milk and other milks with a lactic acid bacterium or co-fermenting it with a lactic acid bacterium and a yeast.

The lactic acid bacteria for use in the present invention are not particularly limited as long as the active ingredient of the present invention can be provided, and they can be selected from known available lactic acid bacteria. Examples of the lactic acid bacteria include those which belong to the genera Streptococcus, Lactococcus, Lactobacillus, and Bifidobacterium. Specific examples include *Streptococcus thermophilus, Lactococcus lactis* (e.g., *Lactococcus lactis* subsp. lacti), *Lactobacillus delbrueckii* (e.g., *Lactobacillus delbrueckii* subsp. bulgaricus), *Lactobacillus helveticus, Lactobacillus casei* (e.g., *Lactobacillus casei* subsp. casei), *Lactobacillus acidophilus, Lactobacillus fermentum, Bifidobacterium longum,* and *Bifidobacterium breve.* More specific examples include *Lactobacillus delbrueckii* subsp. bulgaricus ATCC (American Type Culture Collection) 11842, *Lactobacillus helveticus* ATCC 55796 (corresponding to ATCC 15009), *Lactobacillus casei* subsp. casei ATCC 393, *Lactobacillus acidophilus* ATCC 4356, and *Lactobacillus fermentum* ATCC 14931. Among these, the genus Lactobacillus is preferably used, and *Lactobacillus helveticus* is more preferably used.

The yeasts for use in the present invention are not particularly limited, as long as they have no bad influence on the physiologically functional food of the present invention, and can be selected from known available yeasts. Examples of the yeasts include the genera Saccharomyces, Candida, and Kluyveromyces. Specific examples include *Saccharomyces cerevisiae, Candida utilis,* and *Kluyveromyces marxianus* var. lactis, By carrying out co-fermentation with these yeasts, fragrance can be added to the fermented milk.

With regard to the fermentation method, one or a plurality of the lactic acid bacteria may be cultured in a medium, or one or a plurality of the lactic acid bacteria may be mixed with one or a plurality of the yeast strains and cultured in a medium. As the medium, a medium solely consisting of one or a plurality of the milk components may be used to which may be added secondary components such as yeast extract, vitamins (e.g., ascorbic acid), amino acids (e.g., cysteine), salts (e.g., sodium chloride), saccharides (e.g., glucose, sucrose, oligosaccharides such as raffinose and stachyose), stabilizing agents (e.g., gelatin), and flavors. With regard to the fermentation conditions, the fermented milk or co-fermented milk can be obtained by generally conducting stationary culturing at a fermentation temperature of from 25 to 45° C., preferably from 30 to 40° C. and at an initial fermentation pH of from 6.0 to 7.0 and then terminating the culturing when a cell density reaches at least $10^7$ cells/ml and the medium pH reaches 5.0 or lower, The thus obtained fermented milk or co-fermented milk can be used as the active ingredient of the physiologically functional food of the present invention. The used cells may remain intact or the fermented product may be sterilized by appropriate means such as heating at a temperature of 80° C. Thus, the physiologically functional food which is enriched with a component having brain function-improving, learning ability-enhancing and memory-enhancing functions can be obtained.

The fermented milk or co-fermented milk can be used as the active ingredient of the physiologically functional food of the present invention, as such or as a treated product. Examples of suitable treatment processes include making the fermented milk into a slurry by an appropriate concentration means such as concentration under a reduced pressure or making the milk into a powder by an appropriate means, such as freeze drying and spray drying. In this connection, when powder is obtained, a filler such as dextrin may be added to the milk in order to facilitate formation of the powder. In addition, each of the just described treatment methods may also be applied to a supernatant fluid (whey) obtained by centrifuging the fermented milk or co-fermented milk. Preferably, whey provided by removing curds from the fermented milk or co-fermented milk is used as the physiologically functional food of the present invention.

The physiologically functional food of the present invention can be prepared solely from the active ingredient, namely the fermented milk, the co-fermented milk, a treated product thereof or a mixture thereof, but it may also contain one or more pharmaceutical or nutritionally auxiliary agents. Also, it may contain additives, such as saccharides, proteins, lipids, vitamins, minerals, flavors, and a mixture thereof.

Blending ratio of the active ingredient in the physiologically functional food of the present invention to diluent or auxiliary agent can be any convenient amount, but it is preferably from 5 to 100 w/w %.

The physiologically functional food of the present invention may be used in various forms such as fermented dairy products (e.g., yogurt, lactic acid bacteria beverage), fermented milk-blended processed drinks and foods, tablets, capsules, granules, and food additives.

The physiologically functional food of the present invention can be orally administered to human or animals. In order to obtain brain function-improving, learning ability-enhancing and memory-enhancing functions by administering the physiologically functional food of the present invention, the amount administered may be 0.1 g/kg body weight/day or more as a freeze-dried form of the active ingredient when administered to human.

The physiologically functional food of the present invention is highly safe, because it originates from natural food, and can increase learning ability and memory through improving brain functions by increasing the brain serotonin content. In addition, it is expected to prevent, counter or mitigate senile dementia.

The present invention is now illustrated in greater detail by way of the following examples, but it should be understood that the present invention is not to be construed as being limited thereto.

EXAMPLE 1

A 40 g portion of *Lactobacillus helveticus* ATCC 55796 starter which had been previously cultured was inoculated into 1 kg of skim milk (solid content, about 9% by weight, previously sterilized at 85° C.), and 24 hours of culturing was carried out at 37° C. to obtain a fermented milk. The thus obtained fermented milk was subjected to 30 minutes of centrifugation at 7,000 G to remove solid matter, and a 906 g portion of the resulting supernatant fluid (whey) was freeze-dried yielding 61 g of fermented milk whey powder.

A 6 g portion of the fermented milk whey powder was dissolved in 50 ml of physiological saline (120 mg/ml) and administered by force using an oral sound into the stomach of each of 14 five-week-old male Wistar rats which have been fasted overnight after 1 week of preliminary rearing. The dose was 1.2 g/kg body weight. Two hours after administration, each rat was sacrificed using a guillotine, the brain was excised and subsequently extracted with 1 ml of 0.1 N perchloric acid and centrifuged at 13,000 G for 15 minutes. The resulting supernatant fluid was analyzed using an HPLC to measure amounts of serotonin (5-hydroxytryptamine: to be referred to as "5-HT" hereinafter) in the brain, its metabolite 5-hydroxyindole acetic acid (to be referred to as "5-HIAA" hereinafter) and total 5-hydroxyindole (to be referred to as "5-HIs" hereinafter) as the total of 5-HT and 5-HIAA. A silica reverse phase column manufactured by Japan Spectroscopic (trade name, Catechol Pack) was used as the HPLC column, and an electrochemical detector manufactured by esa (trade name, Coulochem) was used as the detector. As a control, a group of Wistar rats in which physiological saline alone was administered using an oral sound was prepared to carry out the same test. In the following, the fermented milk whey powder-administered group was called sample group, and the physiological saline-administered group was called a control group. The results are shown in FIGS. 1 to 3.

Figure 2:
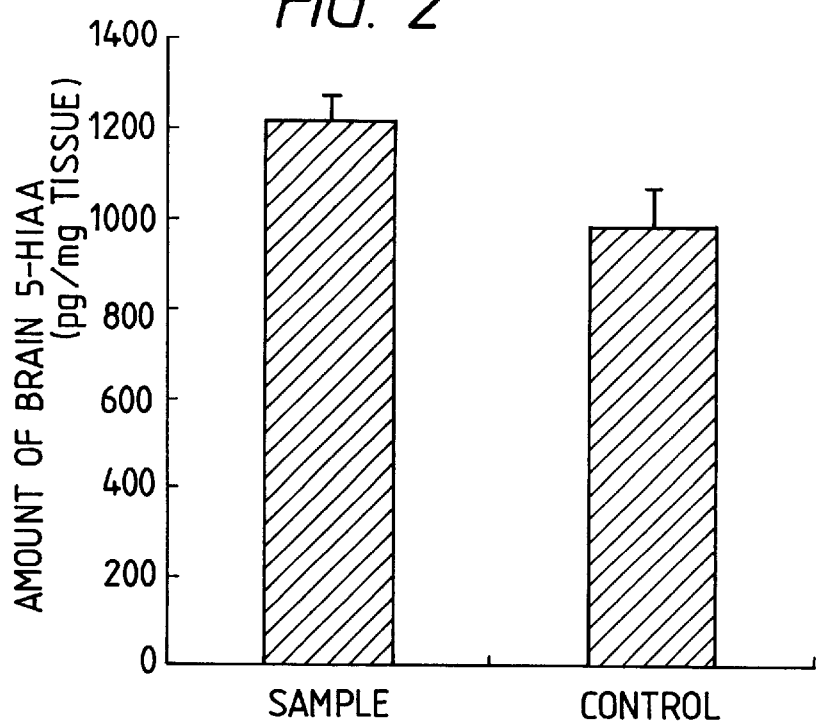
FIG. 2 is a graph of brain 5-hydroxyindole acetic acid content in sample and control groups in Example 1.

The results in FIGS. 1 to 3 show that increases in the amount of brain 5-HT, 5-HIAA and 5-HIs were observed in the sample group in comparison with the control group. Particularly, the amount of 5-HT and 5-HIs in the sample group increased significantly with a level of significance of 5% in comparison with the control group (shown by the mark * in FIGS. 1 and 3). On the basis of the above results, it was confirmed that oral ingestion of the fermented milk whey powder increases the amount of serotonin which is a brain neurotransmitter.

EXAMPLE 2

Three-week-old male Wistar rats were reared for 13 weeks using a test feed, having the composition shown in Table 1, which was mixed with the fermented milk whey powder obtained in Example 1. Thereafter, each rat was put into an individual rearing cage, reared with a controlled feed and then subjected to shaping to carry out 30 days of testing using the following method. Each animal reared with a controlled feed was put into a soundproof shaded scanner box. A 40 mg portion of pellet was given as a feed reward when a lever in the scanner box was pushed at the time of lighting of a lamp in the box. This was defined as a correct response reaction. On the other hand the feed was not given when the lever was pushed during no lighting. This was defined as an incorrect response reaction. Hereinafter, the number of the correct response reactions is abbreviated to $R^+$, and the number of the incorrect response reactions to $R^-$. The test was carried out 40 times a day with each lighting period of 15 seconds, and the learning effect was judged based on a correct response ratio (%) of $(R^+/(R^++R^-)) \times 100$. The memory ability was examined by repeating this test every day. As a control, the same test was carried out using rats reared with a control feed having only the composition shown in Table 1. The results are shown in FIGS. 4 to 6.

TABLE 1

Feed Composition

|  | Test feed | Control feed |
| --- | --- | --- |
| Fermented milk whey powder | 10% | — |
| Separated soybean protein | 16% | 10% |
| Mineral mixture | 4% | 4% |
| Vitamin mixture | 1% | 1% |
| Corn oil | 5% | 4% |
| Cellulose | 5% | 5% |
| Starch (α-starch:sucrose = 2:1) | 66% | 76% |
| Total | 100% | 100% |

Periodical changes in the reaction in the test feed group and control feed group are shown in FIG. 5 and FIG. 6, respectively. In the initial stage of the test, $R^+$ and $R^-$ have almost the same number in both groups. The number of $R^+$ increases in both groups as the repetition of the test increases. In the test feed group, $R^-$ decreased gradually starting on around the 6th day and sharply decreased on and after the 21st day. In the control feed group, on the other hand, $R^-$ hardly decreased and $R^+$ showed similar degree to that in the test feed group, so that the correct response ratio became high in the test feed group in comparison with the control feed group. Particularly, as shown in FIG. 4, the correct response ratio in the test feed group reached 80% on and after the 23rd day of the test, thus showing a significantly higher correct response ratio, with a level of significance of 5%, in comparison with the correct response ratio in the control group (shown by the mark *). In other words, in the test feed group in which a feed supplemented with the fermented milk whey powder was used, the animals learn that they can obtain feed when they push the lever while the lamp was lit and remember this learning without forgetting it for many days. On the basis of the above results, it was confirmed that the fermented milk whey powder significantly enhances learning effect and memory ability in the brightness-discrimination learning behavior test.

EXAMPLE 3

A 40 g portion of Lactobacillus helveticus ATCC 55796 starter which had been previously cultured was inoculated into 1 kg of skim milk (solid content, about 9% by weight, sterilized at 85° C.), and 24 hours of culturing was carried out at 37° C. to obtain a fermented milk. The thus obtained fermented milk was freeze-dried to obtain 93 g of fermented milk powder.

A 2.2 g portion of the fermented milk powder was dissolved in 50 ml of physiological saline (44 mg/ml) and administered by force using an oral sound into the stomach of each of 14 five-week-old male Wistar rats which had been fasted overnight after 1 week of preliminary rearing. The dose was 0.44 g/kg body weight. Two hours after administration, each rat was sacrificed using a guillotine, the brain was excised and extracted with 1 ml of 0.1 N perchloric acid and centrifuged at 13,000 G for 15 minutes, The resulting supernatant fluid was analyzed using an HPLC to measure amounts of 5-HT, 5-HIAA and 5-HIs in the brain. A silica reverse phase column manufactured by Japan Spectroscopic (trade name, Catechol Pack) was used as the HPLC column, and an electrochemical detector manufactured by esa (trade name, Coulochem) was used as the detector. As a control, a group of Wistar rats in which physiological saline alone was administered using an oral sound was prepared to carry out the same test. An increase in the amount of 5-HT, 5-HIAA and 5-HIs was observed. On the basis of the above results, it was confirmed that oral ingestion of the fermented milk powder increases the amount of serotonin which is a brain neurotransmitter.

While the invention has been described in detail and with reference to specific embodiments thereof, it will be apparent to one skilled in the art that various changes and modifications can be made therein without departing from the spirit and scope thereof.

What is claimed is:

1. A method for improving brain function or enhancing learning ability or memory comprising administering to a human or animal a physiologically functional food which comprises an affective amount of milk fermented with a lactic acid bacterium, milk co-fermented with a lactic acid bacterium and a yeast or a mixture thereof, wherein the lactic acid bacterium belongs to the genus Lactobacillus.

2. The method as claimed in claim 1, wherein the physiologically functional food is a fermented dairy product, fermented milk-blended processed drink, fermented milk-blended processed food, tablet, capsule, or granule.

3. The method as claimed in claim 1, wherein the effective amount is at least 0.1 g/kg body weight/day.

* * * * *